US010814197B2

(12) United States Patent
Carswell

(10) Patent No.: US 10,814,197 B2
(45) Date of Patent: *Oct. 27, 2020

(54) SYSTEM, METHOD AND APPARATUS FOR IMPROVING HUMAN RESPONSE, SENSITIVITY AND PERFORMANCE

(71) Applicant: Kenith Carswell, Kansas City, KS (US)

(72) Inventor: Kenith Carswell, Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/377,716

(22) Filed: Apr. 8, 2019

(65) Prior Publication Data

US 2019/0231215 A1 Aug. 1, 2019

Related U.S. Application Data

(63) Continuation of application No. 15/130,733, filed on Apr. 15, 2016, now Pat. No. 10,252,132.

(60) Provisional application No. 62/293,038, filed on Feb. 9, 2016, provisional application No. 62/147,968, filed on Apr. 15, 2015.

(51) Int. Cl.
| *A63B 69/00* | (2006.01) |
| *A61B 5/11* | (2006.01) |
| *A63B 71/06* | (2006.01) |
| *A63B 71/02* | (2006.01) |
| *G09B 19/00* | (2006.01) |
| *A61B 5/00* | (2006.01) |
| *A63B 102/18* | (2015.01) |

(52) U.S. Cl.
CPC ........ *A63B 69/0002* (2013.01); *A61B 5/1124* (2013.01); *A63B 71/02* (2013.01); *A63B 71/06* (2013.01); *G09B 19/0038* (2013.01); *A61B 5/1114* (2013.01); *A61B 5/6803* (2013.01); *A63B 2069/0008* (2013.01); *A63B 2102/18* (2015.10)

(58) Field of Classification Search
None
See application file for complete search history.

(56) References Cited

U.S. PATENT DOCUMENTS

| 5,816,951 A | 10/1998 | Hudock |
| 5,890,985 A | 4/1999 | Jenney |

(Continued)

*Primary Examiner* — Jason T Yen
(74) *Attorney, Agent, or Firm* — Lathrop GPM, LLP

(57) ABSTRACT

Systems and methods for improving an individual's response are disclosed. A system for improving an individual's response comprises an item of headwear having a microphone; a speaker; a recording device secured to a front of the item of headwear; an electroencephalogram cap for measuring and recording electrical activity in the individual's brain; and a computing device. The computing device includes machine readable media; an input device; an output device; a communication device for communicating over a network; a processor in data communication with the machine readable media, the input device, and the output device; and electronic instructions that, when executed by the processor, perform steps for causing the speakers to project noise to the individual and actuating the recording device to record the individual's field of view. The microphone allows the individual to communicate, over the network, with a third party.

17 Claims, 13 Drawing Sheets

(56) References Cited

U.S. PATENT DOCUMENTS

| | | | |
|---|---|---|---|
| 6,358,164 B1 * | 3/2002 | Bracewell | A63B 71/0605 |
| | | | 473/454 |
| 7,285,061 B2 | 10/2007 | Wagner | |
| 7,510,493 B2 | 3/2009 | Wagner | |
| 7,670,237 B2 | 3/2010 | Wagner | |
| 7,955,082 B1 | 6/2011 | Gause | |
| 8,387,169 B2 | 3/2013 | Shockman | |
| 2001/0056000 A1 * | 12/2001 | Hori | A63B 63/00 |
| | | | 473/453 |
| 2005/0032581 A1 | 2/2005 | Wagner | |
| 2009/0149281 A1 | 6/2009 | Johnson | |
| 2009/0221928 A1 | 9/2009 | Einav | |
| 2011/0195804 A1 * | 8/2011 | Hixon | A63B 71/022 |
| | | | 473/451 |
| 2012/0204332 A1 | 8/2012 | Shockman | |
| 2016/0267806 A1 | 9/2016 | Hsu | |

* cited by examiner

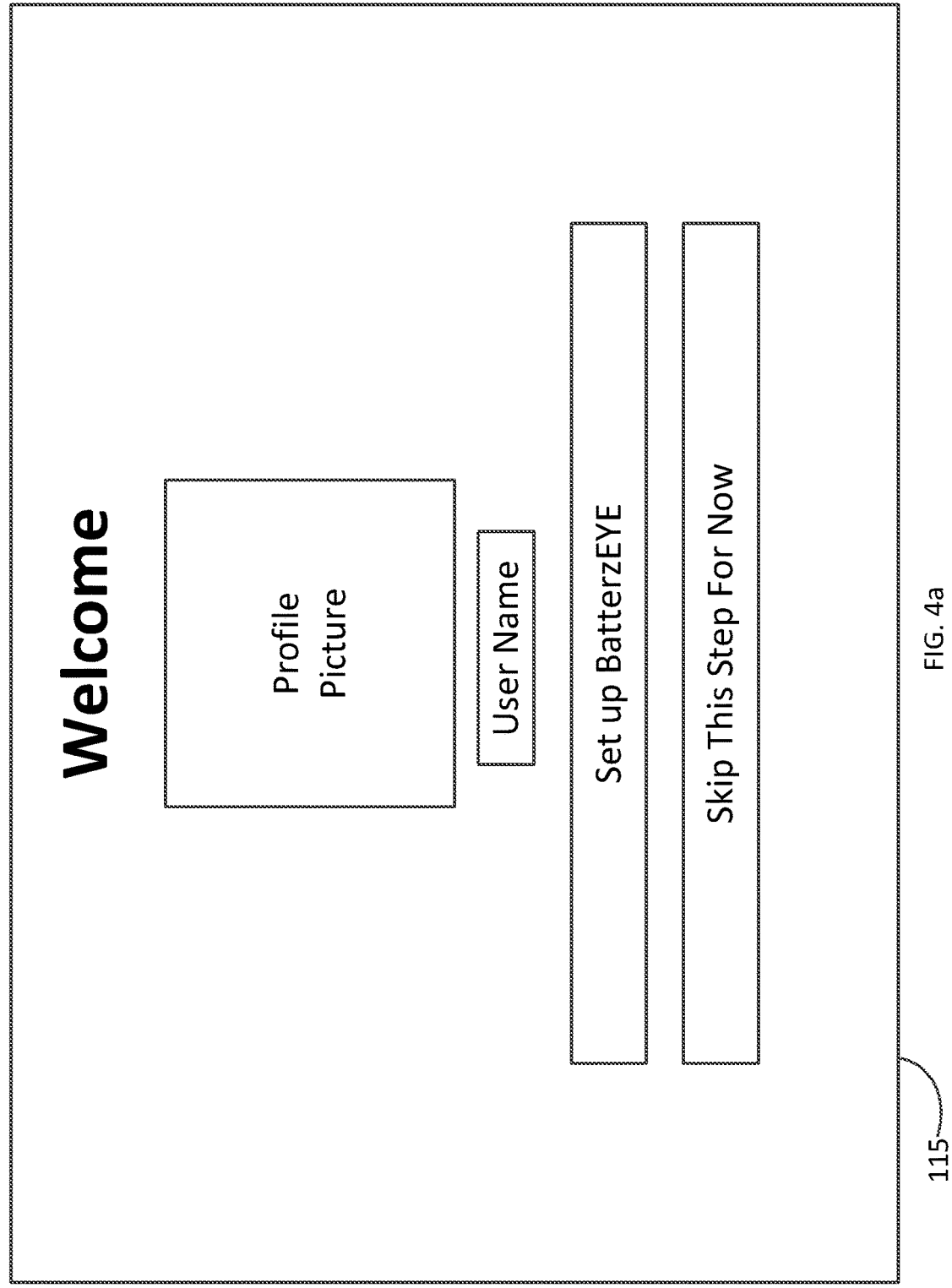

PLAYER SIGN UP

- Profile Image (Uniform Picture)
- Username
- Password
- Name
- E-Mail
- Phone Number
- Date oi Birth
- Zip Code
- Gender: Male / Female

SIGN ME UP

Previous | Next | Done

PLAYER ACADEMIC PROFILE

- Graduation Year
- School: City, State
- Honors Classes
- GPA
- Academic Achievements
- Class Rank
- Intended Course of Study
- ACT/SAT
- Volunteer Efforts
- National Class Rank
- Counselor Student Picture (daily attire)

Additional Picture

Additional Picture

Additional Player Comments (if desired)

Previous | Next | Done

PLAYER STATISTICS PROFILE

| ## | Position | | |
|---|---|---|---|
| | Weight (lbs) | Height (Ft, In) | |

Preferred Bat Model

| Bat Name | Length | Weight |

Bat Used This Session

| Bat Name | Length | Weight |

Bats: L  R  LR

Throws: L  R

Previous  Next          Save          Done

FIG. 4e

PLAYER PERFORMANCE RECORDS

| Swing Goals | Start Date | 11/24/2015 |
| --- | --- | --- |
| Average Swings Per Day | 110 | Total Training Time | 42 hrs |

Batting Average — .390

Exit Velocity — 80 mph

Impact Signature — 110 Db

Training Stage — 1-10

Previous | Next | Done

FIG. 4g

SYSTEM, METHOD AND APPARATUS FOR IMPROVING HUMAN RESPONSE, SENSITIVITY AND PERFORMANCE

RELATED APPLICATIONS

This application is a continuation of U.S. application Ser. No. 15/130,733, filed Apr. 15, 2016 which claims priority to U.S. Provisional Application No. 62/293,038, filed Feb. 9, 2016 and U.S. Provisional Application No. 62/147,968, filed on Apr. 15, 2015, the disclosures of each are incorporated by reference in their entireties.

BACKGROUND

People today are required to perform with increased competency and less margin for error, and in ever more difficult conditions often driven by competitiveness and finances. The ability to quickly process information and maintain supreme control over body, mind, and emotion is as critical as ever, and can require a great deal of sophistication only accomplished by intense skill development. When people do not perform to their ability, their performance is inefficient, and can even be unsafe.

An increased ability to concentrate can benefit persons participating in a variety of activities, including the operation of automobiles, heavy machinery, computers, high-speed vehicles, et cetera. One example wherein increased concentration would be beneficial is in the participation of sports. Athletes utilize different training systems and methods to improve their game. There are a number of these systems that exist, including, for example, the use of pitching machines for batting practice. However, none of the systems and methods currently available is effective for training the player's entire approach to the game. It would be useful to have a training system that athletes can use to train for the game.

SUMMARY

The following presents a simplified summary of the invention in order to provide a basic understanding of some aspects of the invention. This summary is not an extensive overview of the invention. It is not intended to identify critical elements of the invention or to limit the scope of the invention. Its sole purpose is to present some concepts of the invention in a simplified form as a prelude to the more detailed description presented below.

In one embodiment, a system for improving an individual's response includes a distraction system, comprising at least one of the following distraction applications: a system light capable of exhibiting strobe behavior; a speaker; a sensor for determining the stress of the individual; a recording device; an item of headwear; an object delivery device for delivering an object from a first location away from the individual to a second location proximal the individual; and a computing device. The item of headwear is worn by the individual and includes a microphone; a speaker; a recording device secured to a front of the item of headwear; and a device for measuring and recording electrical activity in the individual's brain. The computing device includes machine readable media; an input device; an output device; a communication device for communicating over a network with the distraction system; a processor in data communication with the machine readable media, the input device, and the output device, and electronic instructions that, when executed by the processor, perform steps for: interacting with the individual via a user interface to receive personal data from the individual via the input device; actuating the light and the speaker such that the light exhibits strobe behavior and the speaker projects sound therefrom; actuating the recording device and sensing device to record interaction data of the individual's interaction with the object at the second location; storing the interaction data in the computing device; and providing a readout of the interaction data on the output device. Each of the light, the speaker, the sensor, and the recording device comprise hardware for allowing communication with the computing device over the network.

In another embodiment, a system for improving an individual's response comprises an item of headwear having a microphone; a speaker; a recording device secured to a front of the item of headwear; an electroencephalogram cap for measuring and recording electrical activity in the individual's brain; and a computing device. The computing device includes machine readable media; an input device; an output device; a communication device for communicating over a network; a processor in data communication with the machine readable media, the input device, and the output device; and electronic instructions that, when executed by the processor, perform steps for causing the speakers to project noise to the individual and actuating the recording device to record the individual's field of view. The microphone allows the individual to communicate, over the network, with a third party.

In still another embodiment, a system for improving an individual's response, includes a distraction system and a computing device. The distraction system may include the following distraction applications: a system light capable of exhibiting strobe behavior; a speaker; a sensor for determining the stress of the individual; a recording device; and an item of headwear. The item of headwear may comprise a microphone; a speaker; a recording device secured to a front of the item of headwear; and a device for measuring and recording electrical activity in the individual's brain. The computing device may include machine readable media; an input device; an output device; a communication device for communicating over a network with the distraction system; a processor in data communication with the machine readable media, the input device, and the output device, and electronic instructions that, when executed by the processor, perform steps for: interacting with the individual via a user interface to receive personal data from the individual via the input device; actuating the light and the speaker such that the light exhibits strobe behavior and the speaker projects sound therefrom; actuating the recording device and sensing device to record interaction data of the individual's interaction with the system; storing the interaction data in the computing device; and providing a readout of the interaction data on the output device. Each of the light, the speaker, the sensor, and the recording device comprise hardware for allowing communication with the computing device over the network.

BRIEF DESCRIPTION OF THE DRAWINGS

FIGS. 4a, 4b, 4c, 4d, 4e, 4f, 4h, and 4g illustrate a user interface according to one embodiment of the invention.

DETAILED DESCRIPTION

Research suggests that humans are capable of increasing their senses, for example, vision, by engaging in activities that require intense concentration on a particular item while surrounded by distractions. Employing various distractions while requiring a person to focus intently on a particular item may allow the person to adapt his brain's perception of information and therefore his response to stimulus. It is this ability to practice intense concentration which may allow the operator to experience increased visual perception, balance, anticipation, reaction, et cetera.

Embodiments of systems and methods for improving human response, sensitivity, and performance are disclosed herein. The system may incorporate various distracting mechanisms or applications, described in detail below, which may require the user to practice intense concentration in order to maintain focus on a particular item. The system may further train an individual to control his or her emotions in high pressure situations. While the systems and methods described herein may be beneficial for use to increase a person's concentration in a variety of circumstances, for ease of describing the invention, the description provided herein is directed to the system's use in athletic training, and in particular, in training baseball players to better focus on a baseball to increase the player's ability to consistently perform quality at-bats.

As will be evident based on the description herein, one exemplary object of the invention is to provide a system that places variable stresses on the user in order to create an environment that inhibits concentration (e.g., the opposite of what would typically be considered an "ideal" learning environment). A user of the system is required to exhibit increased focus in order to concentrate on an particular task or object.

Figure 1:
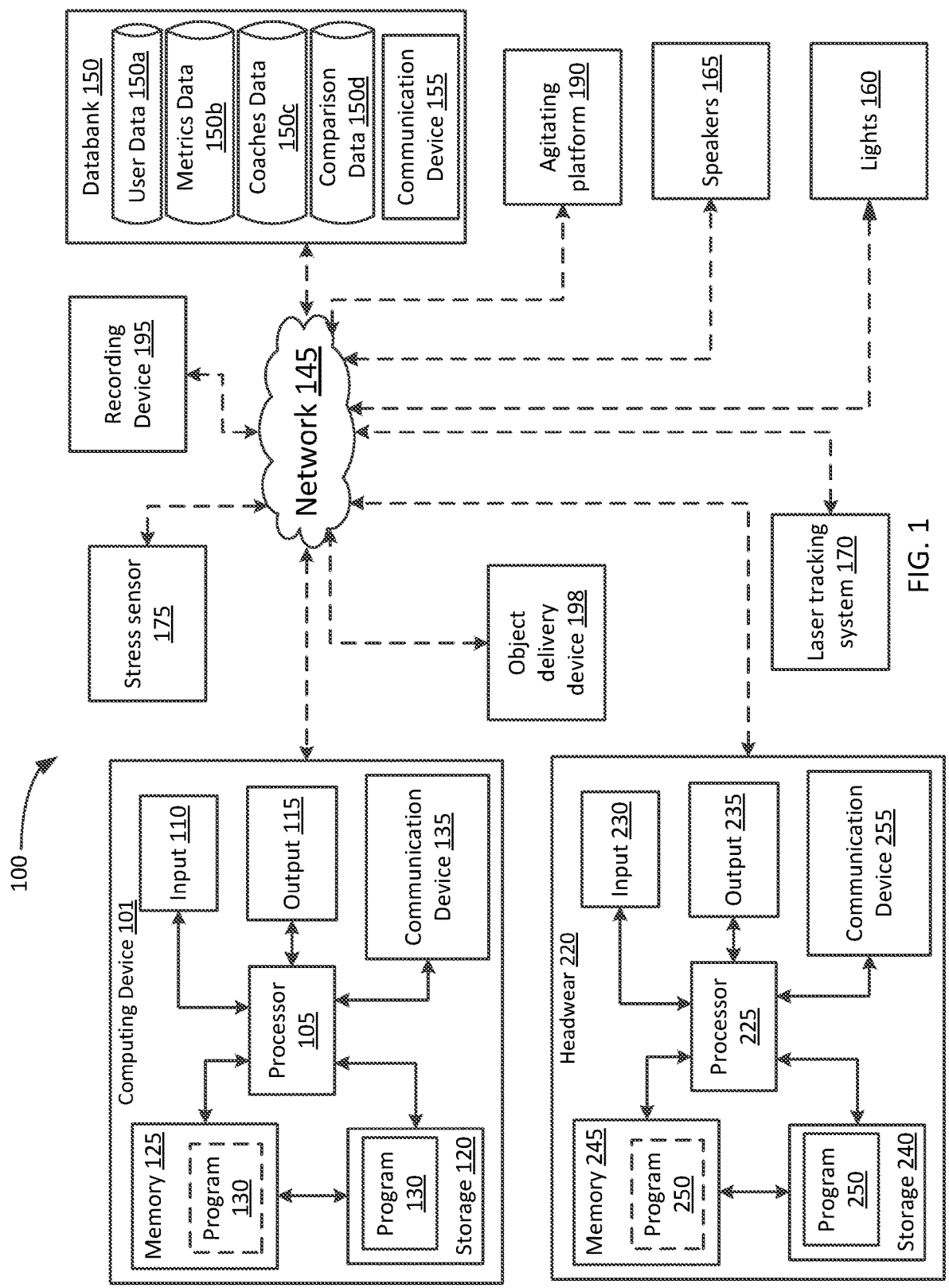
FIG. 1 illustrates an embodiment of a system for improving human response, sensitivity, and performance according to one embodiment of the invention.

Referring initially to FIG. 1, in one embodiment of the invention, a system 100 for improving human performance may include a one or more computing devices 101. The system 100 may further include one or more external input and/or output devices (e.g., 160, 165, 175, 190, 195, 220). The external input and/or output devices (e.g., 160, 165, 175, 190, 195, 220) may be in data communication with the computing device 101—for example, over a network 145—as discussed in more detail below.

The computing device 101 may have a processor 105. The processor 105 may be any type of computational circuit, including but not limited to a microprocessor, microcontroller, controller, complex instruction set computing (CISC) microprocessor, reduced instruction set computing (RISC) processor, graphics processor, digital signal process, or any other type of processor or processing circuit capable of performing the desired function. The computing device 101 may further include a storage unit 120, computer memory 125, an input device 110, an output device 115, and a networking or communication device 135, each of which may be in data communication with the processor 105.

In a preferred embodiment, the computing device 101 may be a desktop device, such as a desktop computer, or a mobile device, such as a laptop (e.g., Apple® Macbook, Dell® Ultrabook, HP® Envy, Sony® Vaio), a tablet (e.g., and iPad, Chromebook, Venue, Surface Pro, Nexus), a smart phone (e.g., iPhone, BlackBerry, Samsung® Galaxy), et cetera. For example, in one embodiment, the computing device 101 may be a tablet. In another embodiment, the computing device 101 may be a smart phone. In still another embodiment, the computing device 101 may be a laptop. Although certain devices are referred to herein by name, those skilled in the art shall appreciate that any suitable mobile device, whether now known or later developed, may be utilized in the system. Further, while the system is illustrated and described herein as having a single computing device 101, multiple computing devices 101 may be included in the system 100 in any desirable combination. For example, in one embodiment, the system 100 may include two computing devices 101, one being a laptop, and another being a smart phone. The multiple computing devices 101 may be in communication with each other over the network 145.

Those of skill in the art will further appreciate that the computing device 101 may include an operating system, such as Microsoft® Windows, Mac® OS, UNIX® OS, Linux® OS, Android OS, for example, which controls basic tasks such as the control and allocation of memory, facilitation of networking, file management, prioritization of processes, et cetera.

The storage unit 120 may be, for example, a disk drive for storing programs and data, and the storage unit 120 is shown having an application or program 130 for controlling a distracting environment as set forth below. As is understood by those of skill in the art, the program 130 can be broken into one or more subprograms, which may be stored in storage units 120 of separate devices 101. Data may be transferred between storage units 120 using known methods. The application 130 may be permanently or temporarily stored in the computer memory 125, which may be transferred thereto from the storage unit 120.

The input device 110 and the output device 115 may include any device capable of inputting information into, and presenting data from, the computing device 101. For example, the input 110 may comprise one or more keys, switches, knobs, sensors, remote controllers, microphones, stylus pens, cameras, receivers (e.g., RFID or Bluetooth receivers), input slots for CD, DVD, VHS, USB, SD cards, et cetera. In a preferred embodiment, the input 110 may include a wired or wireless keyboard and a mouse. The output device 115 may be a computer monitor, touch screen, or printer, for example. The output device 115 may be useful for displaying a user interface of the program 130, illustrated in FIGS. 4a-4h. The user or administrator may input data into the program 130 via the input device 110, which is displayed to the user or administrator via the output device 115.

The networking device 135 may be any networking device that allows the computing device 101 to connect to the network 145, such as a switch, router, modem, networking card, antenna, transceiver, et cetera. The network 145 may be any suitable network that allows for bidirectional communication between the computing device(s) 101 and the external input and/or output devices (e.g., 160, 165, 175, 190, 195, 220). For example, the network 145 may be one or more of a wireless (or wired) wide area network, a local area network, a personal area network, a cellular network (e.g., GSM or CDMA), a Bluetooth network, and infrared network, the World Wide Web, et cetera.

In some embodiments, the system 100 may include a solitary server, computer (e.g., a desktop or laptop computer), or other suitable computing device. In other embodiments, the system 100 may include a collection of servers, computers, or other suitable computing devices. Typically, a cluster or collection of servers may be used when the demands of the external input and/or output devices are beyond the reasonable capabilities of a single server or computer. In some embodiments, the servers in the cluster or collection of servers may be interchangeable from the perspective of the external input and/or output devices (e.g., 160, 165, 175, 190, 195, 220).

The system 100 may optionally further include additional memory capability, such as a databank 150. The databank 150 may be communication (e.g., over the network 145) with the computing device 101 and the various external input and/or output devices (e.g., 160, 165, 175, 190, 195, 220). The databank 150 may comprise a plurality of databases. For example, as shown in FIG. 1, the databank 150 may include a user data database 150a, a metrics data database 150b, a coach database 150c, and a comparison data database 150d.

The user data database 150a may store information about each player in a player profile, for example. This information may include a player's name, birthday, height, weight, and potentially even career statistics. The metrics database 150b may store information regarding the player's results with the system 100, or metrics related to an entire team, for example. The coaches database 150c may store information about coaches, which may include name, institution where he or she coaches, and contact information. The comparison database 150d may store results as compared with other users of the system.

The various databases 150a, 150b, 150c, and 150d may be accessed by the user, a coach, or an administrator, depending on the level of security placed on the program 130. The user (e.g., a player) may wish for coaches to be able to access their personal and metrics information, and coaches may desire for the players to be able to access their information. However, the coach may not wish to provide personal information (e.g., home phone number) to the players, and therefore this information may be hidden from the player.

As noted above, the external input and/or output devices (e.g., 160, 165, 175, 190, 195, 220) may be chosen from a number of different devices, described below. Additionally, it will be understood that more than one of the external input and/or output devices (e.g., 160, 165, 175, 190, 195, 220) may be included in a combination as part of the system 100, and the devices may be configured to communicate with each other and the computing device 101, for example, over the network 145.

In one embodiment, an output device comprises one or more lights 160. The lights 160 may be any type of light that, when lit, would cause distractions for the user of the system 100. For example, the lights 160 may be UV lights, LEDs, LCDs, lasers, et cetera. Further, the lights 160 may be strobe lights, dance floor lights, or any other type of flashing or discontinuous lighting application. As described below, in a preferred embodiment, the lights 160 are provided as LED strobe lights.

Figure 2:
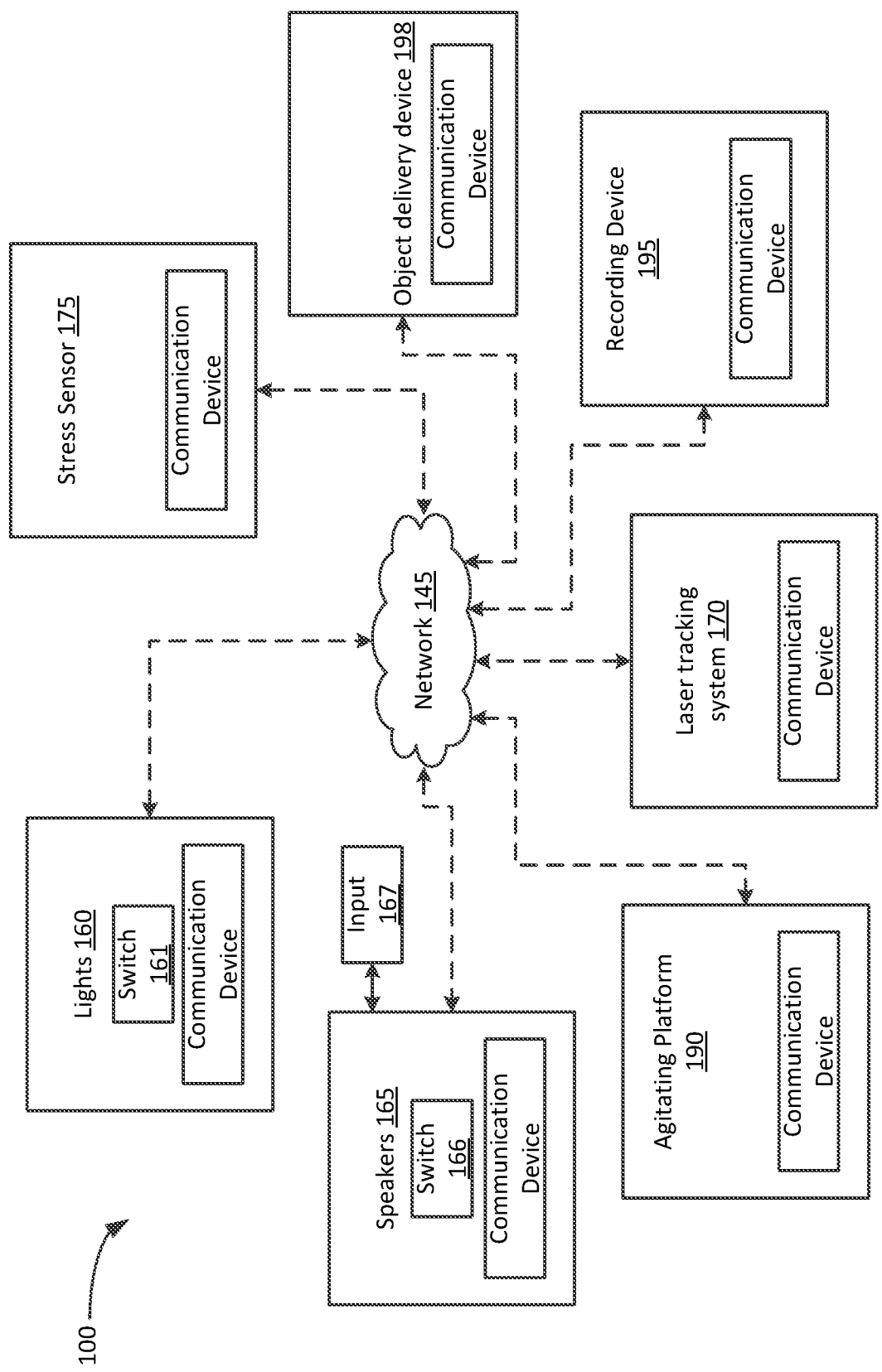
FIG. 2 illustrates various apparatus for creating a distracting environment according to the system of FIG. 1.

The lights 160 may be in wired or wireless communication (e.g., over the network 145) with the computing device 101 such that operation of the program 130 controls the operation of the lights 160. Alternatively, the lights 160 may be controlled with a simple switch 161 (FIG. 2) for controlling the flashing and/or the brightness of the lights 160.

The lights 160 may comprise one or more of the types of lights listed above. In one preferred embodiment, the lights comprise 8-foot LED lights. However, other lengths of LED light bars may additionally, or alternatively, be included in the system (e.g., 6-foot LED bars, 4-foot LED bars, etc.). Typically, LED lights are provided in an array and attached to a circuit with a driver. The LED driver converts higher voltage, alternating current to low voltage, direct current, as most LEDs are designed to run on low voltage (e.g., 12-24V), direct current electricity, and most places supply higher voltage (e.g. 120-277V) alternating current electricity.

Due to the drivers that are usually employed with LED lights, typical 8-foot LED lights do not have the capability to perform as strobe lights (e.g., flashing). However, removing the driver from the 8-foot LED and re-programming the printed circuit board (PCB) may allow the lights to be customized so as to exhibit strobe behavior. For example, the LED lights may be electrically connected a control box having a customized PCB, AC/DC controller, and power step chip set for controlling the strobe function of the LED lights. The PCB may be programmed with one or more algorithms according to known methods to cause the lights to strobe at various intervals. The algorithms may allow the lights to flash in such a manner so as to simulate, among other things, different speeds of pitches and different types of pitches (curve ball, fast ball, slider, etc.). Similar technology may additionally be employed with the other types of lights, either alone or in combination with the LED lights.

The light 160 may comprises a plurality of LED lights arranged on a circuit board in any configuration. In one configuration, the plurality of LED lights are configured as a square wave, and a controller is electrically coupled to the plurality of LED lights and is operable to operate the LED lights in a mode in which the LED lights flash in a predetermined sequence. The predetermined sequence may be selected to simulate various speeds of pitches. The circuit board may include a digital readout which may allow an administrator to alter the sequence to change how the player perceives the baseball as it is being thrown to the player.

Whether the lights 160 are controlled via operation of the program 130 over the network 145 or through operation of a switch 161, the user may be provided with a readout (e.g., via output device 115) of the strobe level of the lights 160 during his or her particular session. The results may be communicated (e.g., over the network 145) and stored in the memory 125 or a databank 150 for future reference. Alternately, the results may be independently input (e.g., via input 110, such as a keyboard) into the computing device 101. By keeping track of the strobe level of the lights, the hitter may be able to determine his or her accuracy of detecting ball replication.

In order to maximize the effects of the lighting 160, extraneous lights, such as those provided for general lighting purposes of the building or practice area, may be turned off such that the environment is dark when the lighting 160 is not activated. Objects that are desired to be seen may be equipped with glow-in-the-dark features to make them visible in the dark. Black lights may be placed around the area so as to enable the glow-in-the-dark features to be seen in the dark. For example, while one objective of the system is to make it difficult for a user to focus on a particular object (e.g., a baseball) in order to require the user to exercise greater focus and concentration, it may be beneficial for the object to be at least somewhat visible during the periods of darkness. This may be especially true at a beginner's level. Therefore, it may be desirable for the threads on the baseball to be glow-in-the-dark such that the user may be able to track the ball during periods of darkness (e.g., when the lights are flashing between periods of lesser and greater illumination) from the time the baseball leaves the "pitcher" until it reaches home plate, at which time the user hopefully makes contact with the ball. As the user becomes more adept at tracking the baseball, the user may desire a baseball that does not have glow-in-the-dark features, thus requiring even greater focus and concentration in order to hit the ball.

In another embodiment, the extraneous lights may be extinguished, and UV lights may be illuminated. The baseball may be equipped with laces (or seams) having glow-in-the-dark capabilities. Thus, the batter may only see the laces of the baseball as it travels from the "pitcher" to home plate.

If the lights 160 are in communication with the computing device 101, operation of the program 130 may cause the lights 160 to flash or otherwise shift between periods of lesser and greater illumination according to random time intervals. Alternatively (or additionally), the program 130 may cause the lights 160 to flash in accordance with the beat of a song, for example. Accordingly, it may also be desirable for the system 100 to include one or more speakers 165. The speakers 165 may be in wired or wireless communication (e.g., over the network 145) with the computing device 101, which may control the operation of the speakers 165. The program 130 may include a timer to allow the speakers 165 to play a particular song, or series of songs. The program 130 may also be configured to cause the speakers 165 to play other distracting noises, such as beeping noises, white noise, or any other sound, especially those sounds which may be associated with a particular activity (e.g., cheering, booing, crowd noise, announcements, etc.).

The level of sound through the speakers 165 may oscillate randomly (e.g., from a reduced level to an amplified level) as a result of operation of the program 130, which may include various subprograms for controlling the sound in the speakers 165, for example, according to various patterns. The program 130 may also be configured keep the level of sound constant throughout the operation.

In one example, a beginner level user or the administrator may select a subprogram that plays a single distracting noise (e.g., crowd noise) at a constant level for a desired period (e.g., the length of one practice, or at various intervals). As the individual advances, the alternative subprograms may cause the distracting noises to be randomly selected and played, and the level of sound to oscillate between reduced and amplified levels.

Alternately (or additionally), controlling the level of sound may be accomplished by physically operating a volume control (e.g., switch 166, FIG. 2) so as to turn the volume up or down, as desired. Further, the speakers 165 may be configured to receive an input 167 from a personal device, for example, a cell phone, tablet computer, etc. The input 167 may provide the sound and control the level of noise emanating from the speakers 165.

The lights 160 and/or speakers 165 may be positioned around the learning area (e.g., the batting cage) to provide distractions from multiple positions around the user. It shall be noted that the lights 160 and/or speakers 165 may be transportable such that they may be positioned in myriad different positions and locations based on the needs and desires of a particular user. Alternately, the lights 160 and/or speakers 165 may be permanently fixed in a desired position, which may be determined to be the most effective placement of the equipment.

In still another embodiment, the system 100 may include means for measuring and/or recording an individual's level of stress while utilizing the system (e.g., stress sensor 175). For example, the system 100 may include a heart rate monitor which may be temporarily fixed to the user and configured for wireless communication with the computing device 101 (e.g., over the network 145). One exemplary device for measuring heart rate may include a glove (e.g., a batter's glove) which is worn by the user during the session. The glove may utilize electrodermal activity (EDA), also known as galvanic skin response technology, to measure the individual's heart rate. The individual's heart rate data may be transferred (e.g., over the network 145) to the computing device 101 or the databank 150. At the end of the session, the individual may receive a readout of his or her heart rate during the session (e.g., via output 115). This may allow the individual to pinpoint situations that cause excess stress to the individual, which may then allow the individual to address these situations in order to maintain a calm demeanor.

Comparing heart rate data over a period of time, such as several sessions, may allow the individual to quantify the results of using the system 100. For example, the individual may find that when he first began using the system 100, his heart rate was elevated (indicating a high level of stress) when there was a lot of noise. As the user became more comfortable with blocking out the distractions as a result of training using the system 100 described herein, his heart rate began to stabilize, indicating that the user has increased confidence hitting the ball during increased levels of noise.

In another embodiment, the system 100 may further include additional apparatus for distracting the user of the system 100, for example, at the user's position of engagement with the system 100. In one example, the system 100 may be equipped with a platform 190 upon which the user stands while engaging with the system 100. The platform 190 may be configured to vibrate or otherwise move back and forth during the user's engagement with the system 100. Consequently, the platform 190 may be equipped with hydraulics or other means for causing the platform 190 to move. As described above regarding the lights 160 and speakers 165, the platform 190 may be in communication with the computing device 101 for controlling the movement of the platform 190. Operation of the program 130 may cause the platform 190 to move randomly backwards and forwards, and/or to provide vibration. The user may thus be forced to maintain focus and stance even while being involuntarily moved. Continuing with the baseball example, the home plate and corresponding batter's boxes may be positioned atop the platform 190. The user may take his or her place in the appropriate batter's box, and prepare to receive pitches. The program 130 may then cause the platform 190 to move, requiring intense concentration by the hitter in order to maintain focus on the baseball and maintain a correct batting stance.

In addition to providing a distracting environment, it may be beneficial to provide apparatus 195 for tracking an individual's performance in order to provide evaluations and/or feedback to the individual. For example, various recording apparatus 195, such as cameras, video recorders, drones equipped with cameras to capture specific camera angels, microphones, or other recording devices may be provided to measure, record, and optionally display (via output 115, for example) quantifiable results of the individuals' performance. The apparatus 195 may be in communication (e.g., over the network 145) with the computing device 101 and data received therefrom may be stored in the databank 150. The program 130 may be configured to use the data from the recording apparatus 195 to rate multiple users based on performance and/or improvement.

One example of an apparatus 195 for tracking performance may include a microphone located on or near home plate. The microphone may be able to record the sound of the ball coming off of the bat, which may be directly related to how well the batter hit the baseball.

Figure 5:
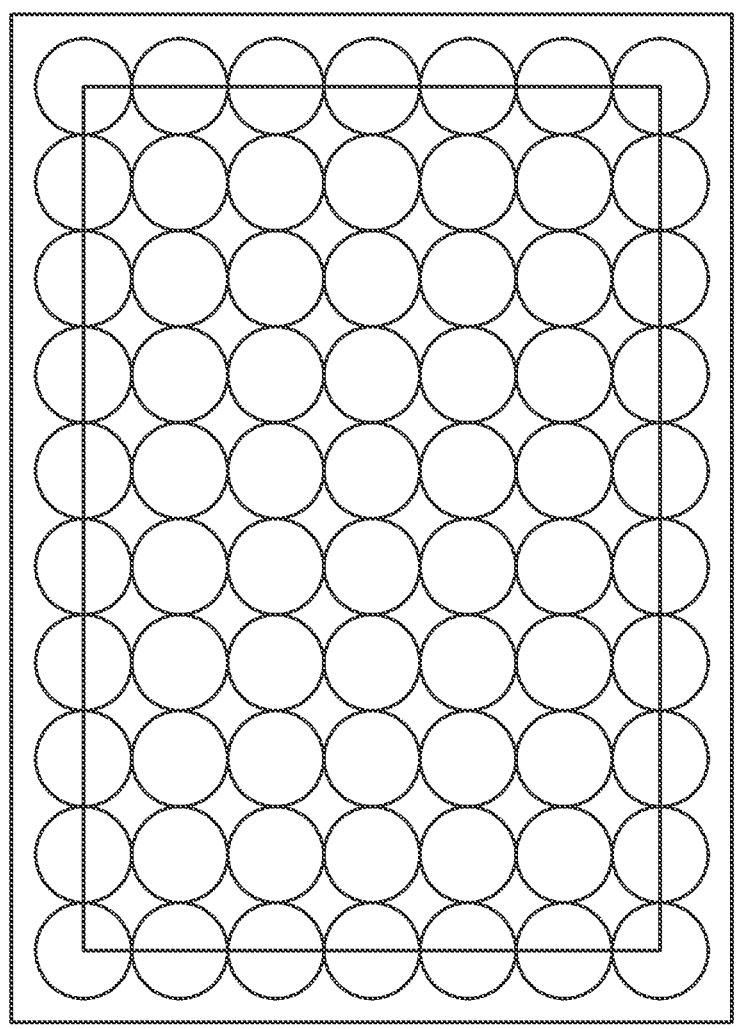
FIG. 5 illustrates an exemplary strike zone, according to one embodiment of the invention.

In a further example, the system 100 may be equipped with a laser tracking system 170 for tracking where in the strike zone the individual has the greatest strength and weakness. An exemplary strike zone is illustrated in FIG. 5. The strike zone is always the width of an official or regulation size home plate. In one embodiment, the strike zone is seven baseball widths across. In another embodiment, the strike zone is 17" across. However, the height of the strike zone depends on the height of the hitter. As described herein, the program 130 may be individually tailored for each user of the system. Therefore, when the individual inputs his or her information into the program 130, the person's strike zone may then be determined.

In another embodiment, it may be desirable for the user to see targets outside of the strike zone. Therefore, the laser tracking system 170 may be further configured to provide targets where are outside the strike zone.

The laser tracking system 170 may include, for example, a laser mounting device. The laser mounting device may comprise a standing having vertical legs and a horizontal axis extending therebetween. Lasers may be positioned along the vertical and horizontal legs. The laser mounting device may be positioned just ahead of the hitter's anticipated contact area such that the lasers are able to project the hitter's strike zone in the hitter's field of view. In one embodiment, a vapor screen may be further incorporated into the system 100 for projecting the strike zone and/or other visual distractions. The strike zone may be provided in 1-dimension or 3-dimensions, depending on the hitter's preference or requirements.

As the hitter hits the baseball, additional lasers (or other tracking device, such as a camera or video camera) may be placed outside of the hitting zone (e.g., on a mounting device) and may be configured to track and/or record where the baseball was located in the strike zone, and whether the batter made contact with the ball. The batter's hitting information may be aggregated into a chart to show areas of strength and weakness within the strike zone.

In yet another embodiment of the invention, the system 100 includes a helmet 220 (or other type of protective headgear). The helmet 220 may be, for example, a traditional helmet typically worn by athletes for a respective sport, which has been equipped with various capabilities for creating a distracting environment and/or means for collecting, storing, and transferring data. The helmet 220 may be in communication with the computing device 101, for example, over the network 145. Alternatively, the helmet 220 may be fully capable of acting alone. The helmet 220 may thus include a computing device 201 having a processor 225, storage 240, memory 245, a program 250, one or more input and output devices 230 and 250, respectively, and a communication device 255 for communicating over the network 145.

The helmet 220 may include various distraction-inducing capabilities (e.g., output devices 250), as well as means for collecting and transferring data. In one embodiment, the helmet 220 is equipped with speakers which may provide audio distraction to the helmet wearer. The helmet 220 may receive the audio input from the computing device 101 or the helmet computing device 201 (which may include various audio files in the storage 240 for playback over the speakers), or from an input device 230 (such as a cell phone, iPod, MP3 player, SD Card, et cetera).

The helmet 220 may additional include a microphone. The player may be able to communicate with an administrator, for example, via the microphone using existing technology, such as Bluetooth or cellular technology, or by transmitting the audio over the network 145.

The helmet 220 may include a camera or video recorder for taking pictures and/or videos of the user's view during the session. The camera and/or video recorder may allow the user to track the position of his or her head during a pitch cycle. It may be preferable for the camera to be located, for example, between the user's eyes at a position that does not obstruct the user's view. This video may be stored in the memory 245, or alternately transmitted over the network 145 and stored in the memory of the computing device 101, or in the databank 150.

In addition to speakers and cameras, the helmet 220 may include an accelerometer and/or a gyroscope. The accelerometer and/or gyroscope may further monitor the position of the user's head during a pitch cycle, for example (or, in another example, as a golfer swings his clubs). The accelerometer and/or gyroscope may collect data of the user's head position at predetermined intervals (e.g., every ½ second, every second, every two seconds, etc.) The data may be stored in the helmet's memory 245, or may be transmitted to the computing device 101 or stored in the databank 150.

The helmet 220 may be further equipped with sensors. The sensors may be useful for determining a force exerted upon the helmet 220, among other uses. Unfortunately, sports have an inherent level of a risk of injury. In baseball, helmets are required to be worn by batters to prevent baseballs from hitting a batter directly on the head, the results of which could be catastrophic. It may be desirable to know what forces are exerted on the helmet 220 (and therefore, on a person's head) so as to provide additional data in determining the health of the batter.

The helmet 220 may additionally include means for measuring brain activity during the session. Using known technology, such as electroencephalogram technology, the administrator may be able to monitor electrical activity in the brain. This information may be stored in the databank 150, and may be further provided to the user at the end of the session (e.g., via output 115).

Operation of various apparatus in the helmet 220 may cause the wearer of the helmet 220 to experience heightened temperatures. The helmet 220 may thus be equipped with cooling technology, such as a Peltier Thermoelectric Cooler. Other cooling technology may also, or alternatively, be incorporated into the helmet 220.

As may be understood by those of skill in the art, the helmet 220 may be a standalone piece of equipment, or alternately, may be provided in conjunction with one or more of the various applications discussed above (e.g., lights 160, speakers 165, platform 190, etc.). Information retrieved from the various applications of the helmet 220 may be stored therein (e.g., at memory 245), or transmitted (e.g., over the network 145) to another location for more permanent storage, such as on the databank 150 or memory 125.

The helmet may further include, for example, a GPS locator. This may enable the user to locate his or her helmet, should it become misplaced, or for a parent to locate a child Certain variables that would otherwise exist in the process 100 may be removed, as necessary, to provide a more automated system. For example, an object delivery device 198, such as a pitching machine, may be provided either separately, or in communication with the computing system 101 (e.g., over the network 145), to remove the element of varied pitching as a result of human performance. In this way, the user of the system may be able to more easily quantify the results of his or her performance in a particular session, and perhaps more importantly, over a period of time of using the system.

The system 100 may be further illustrated by another non-limiting example. The system as described above may be implemented as part of a basketball training system. The system may be generally the same as described herein, except as is described below or as would be obvious to one having ordinary skill in the art. Various lighting applications may be positioned at or near the basketball goal to distract the player. Further, auditory and other distractions may additionally or alternately be included as described above.

The basketball goal may be provided in front of, for example, an LCD, LED, or other type of screen which may play various images and/or light patterns to distract the player. The backboard of the basketball goal may be configured to slide laterally along the length of the screen (or beyond the length of the screen) such that the focal point of the backboard shifts. It may thus be preferable for the backboard to be clear such that light and/or other distractions may be transmitted through the backboard. Alternately, the backboard may itself be an LCD, LED, or other type of screen capable of projecting images light patterns while withstanding repeated shocks by basketballs.

Those of skill in the art shall understand that the system 100 may be housed, for example, in a warehouse equipped with the necessary electrical components for running the system 100. Alternately, the system 100 may be portable and may be configured to run on battery, solar, or other type of power.

Figure 3A:
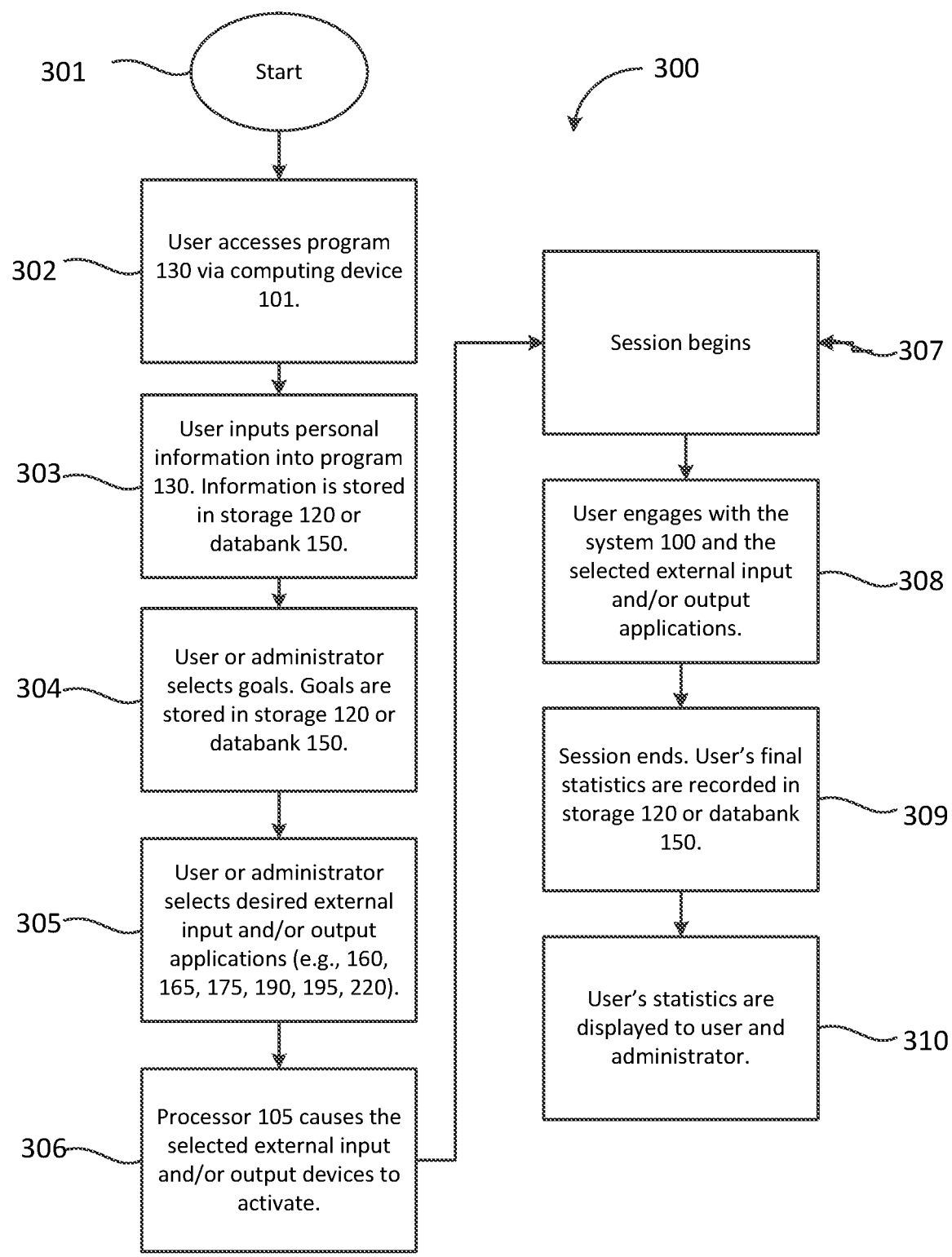
FIG. 3a illustrates a process for improving human response, sensitivity, and performance according to one embodiment of the invention.
Figure 3B:
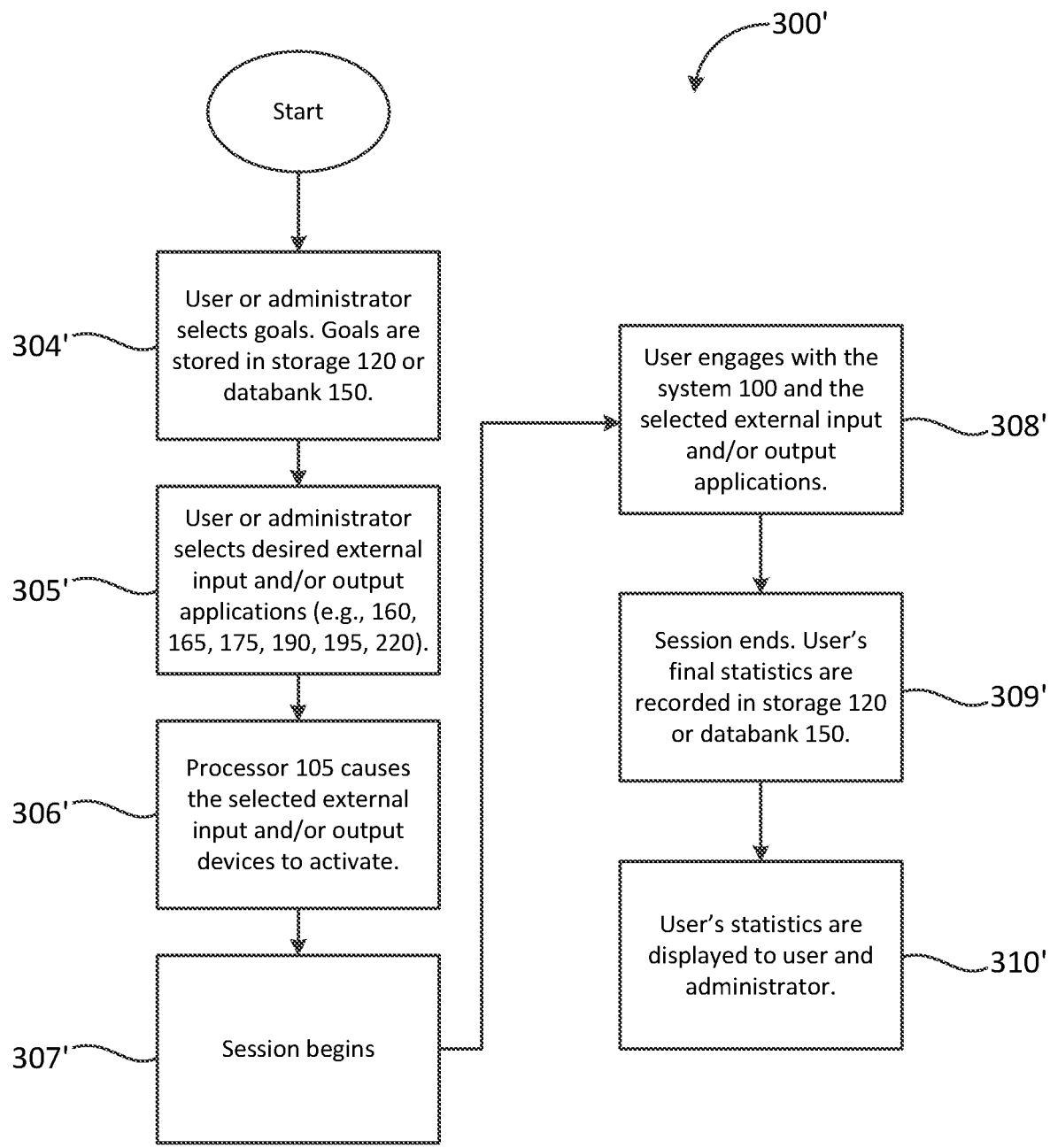
FIG. 3b illustrates process for improving human response, sensitivity, and performance according to another embodiment of the invention.
Figure 4C:
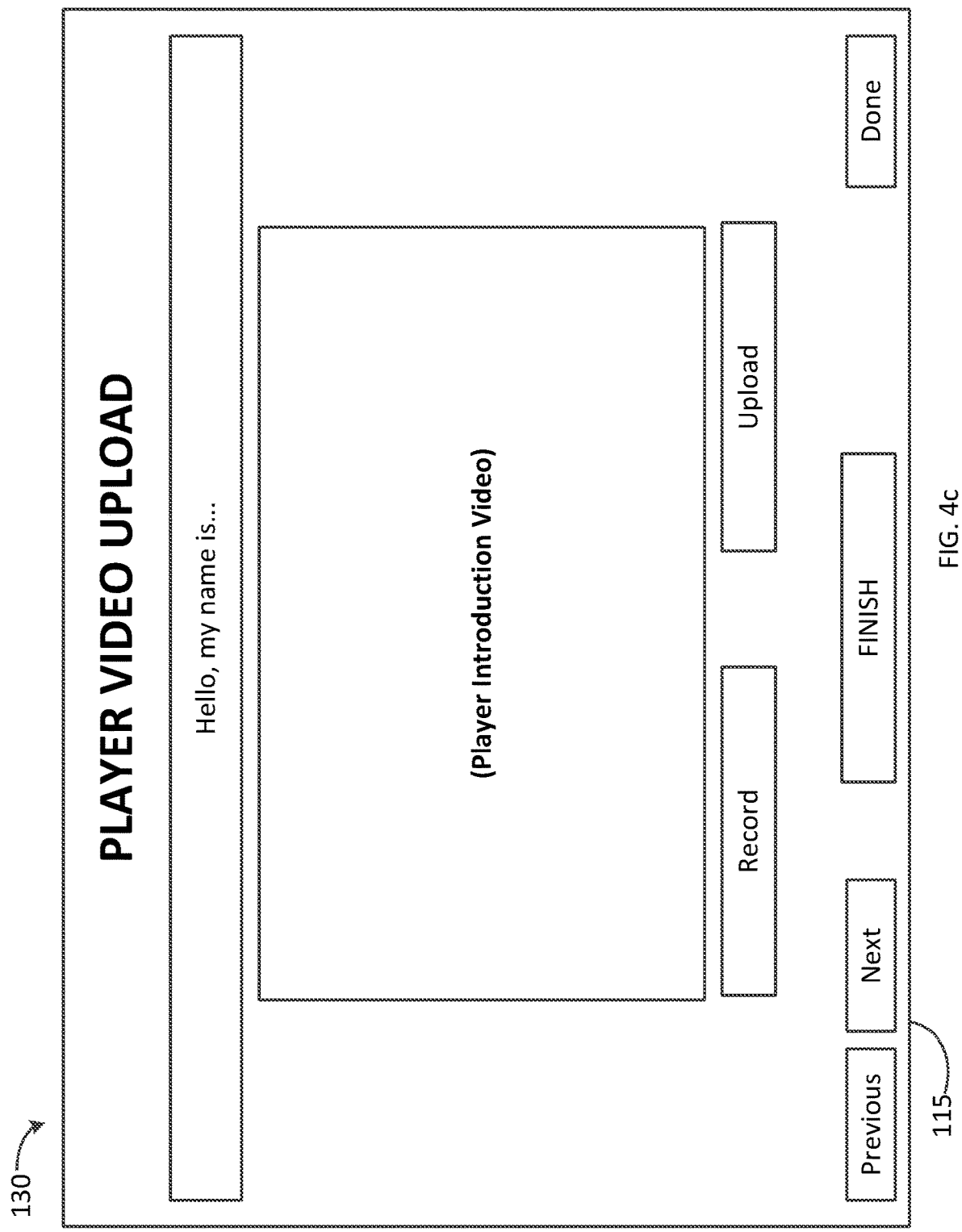
Figure 4F:
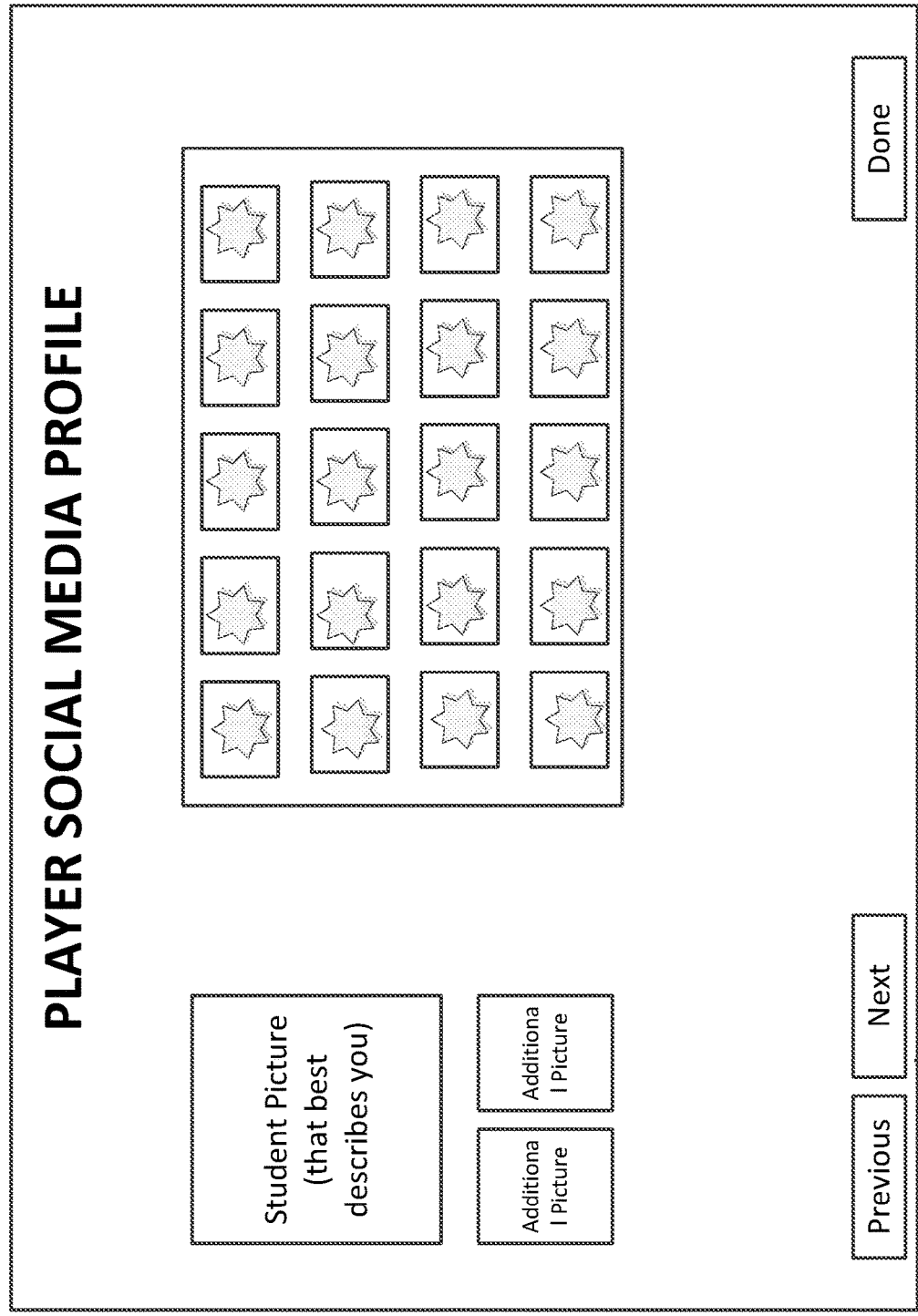
Figure 4H:
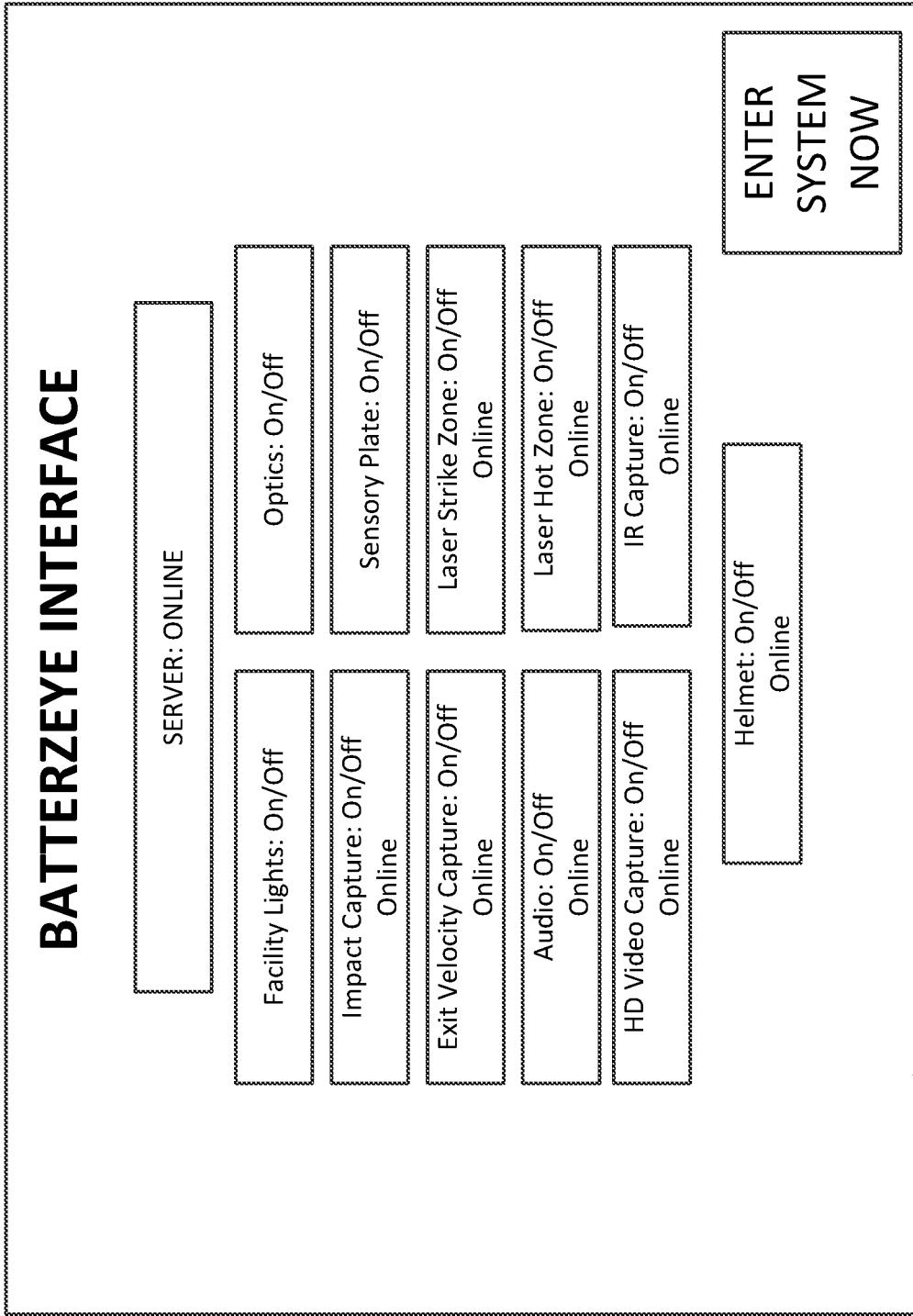

Attention is now directed to FIGS. 3a and 3b, which illustrate a method 300 of operation of the system 100. In FIG. 3, the method 300 begins at step 301. At step 302, the user or administrator accesses the program 130 via the computing device 101, and more particularly, input device 110. At step 303, the user (or administrator) uses the input device 110 to input the user's personal information into the system to create a user profile (see FIGS. 4a-4f). The profile may include the user's name, contact information, player statics, etc. The information may be stored in the computing device memory 125, or the databank 150. The user or administrator may be prompted to provide a desired level of privacy, so that only certain information is available to persons unknown by the user and/or administrator.

At step 304, the user or administrator selects goals for the user (FIG. 4g) and the information is stored in the appropriate storage device. Moving on to step 305, the user or administrator selects the various external input and/or output applications (e.g., 160, 165, 175, 190, 195, 220) that are desired to be in sue during the session. The program 130 may include an option for selecting the player's level of performance (e.g., beginner, intermediate, advanced, custom), and subprograms may be activated based on the chosen skill level for operating the external input and/or output applications.

At step 306, the processor 105 causes the selected external input and/or output applications to activate, and any external input and/or output applications that are not controlled over the network 145 via program 130 may be activated by the user and/or the administrator. The process then continues to step 307.

At step 307, the session begins, and at step 308, the batter receives pitches and the respective applications take, transmit, and/or store data as provided herein. Step 308 may continue for a predetermined period of time (e.g., 30 minutes, 1 hour, 2 hours, etc.).

At step 309, the session ends, and the player's final statistics may be recorded and stored in the databank 150. The player's results may additional be compared to other player's results and stored in the comparison database 150d.

At step 310, the processor 105 causes the output device 115 (e.g., printer or display) to provide the user or administrator with a printout or display of the user's statistics for the session.

FIG. 3b illustrates a truncated process 300' of the process 300 of FIG. 3a. Here, the user may be returning of a second visit. Since the player's information is already stored in the program 130 (e.g., in memory 125 or databank 150), the process 300' may start at step 304', which corresponds to step 304 in FIG. 3a. The process 300' then proceeds through steps 305', 306', 307', 308', 309', and 310', as described above regarding FIG. 3a.

Many different arrangements of the described invention are possible without departing from the spirit and scope of the present invention. Embodiments of the present invention are described herein with the intent to be illustrative rather than restrictive. Alternative embodiments will become apparent to those skilled in the art that do not depart from its scope. A skilled artisan may develop alternative means of implementing the disclosed improvements without departing from the scope of the present invention.

Further, it will be understood that certain features and subcombinations are of utility and may be employed without reference to other features and subcombinations and are contemplated within the scope of the claims. Not all steps listed in the various figures and description need to be carried out in the specific order described. The description should not be restricted to the specific described embodiments.

The invention claimed is:

1. An environmental arrangement for improving a batter's hitting, the environmental arrangement comprising:
   a substantially dark hitting area;
   a substantially dark delivery area from which a ball is delivered to the hitting area;
   a strobe light positioned to output strobing slight visible from the hitting area when the batter looks toward the delivery area and the ball is being delivered to the hitting area;
   a speaker positioned to output sound audible from the hitting area; and
   a computing device comprising:
   machine readable media;
   an input device;
   an output device;
   a processor in data communication with the machine-readable media, the input device, and the output device; and
   electronic instructions that, when executed by the processor, perform steps for at least one task selected from the group consisting of:
     (a) causing the strobe light to output strobing light visible from the hitting area; and
     (b) causing the speaker to output sound audible from the hitting area.

2. The environmental arrangement for improving a batter's hitting of claim 1, further comprising a sensor determining a physiological condition of the individual.

3. The environmental arrangement for improving a batter's hitting of claim 1, wherein the strobe light comprises:

a plurality of LED lights; and a controller electrically coupled to the plurality of LED lights, the controller being operable to operate the plurality of LED lights in a mode in which the plurality of LED lights flash in a predetermined sequence.

4. The environmental arrangement for improving a batter's hitting of claim 3, wherein the strobe light further comprises at least one UV light.

5. The environmental arrangement for improving a batter's hitting of claim 1, further comprising a batting cage, and wherein the hitting area and the delivery area are inside the batting cage.

6. The environmental arrangement for improving a batter's hitting of claim 5, further comprising a pitching machine at the delivery area.

7. The environmental arrangement for improving a batter's hitting of claim 6, wherein the electronic instructions, when executed by the processor, perform steps for each of:
  (a) causing the strobe light to output strobing light visible from the hitting area; and
  (b) causing the speaker to output sound audible from the hitting area; and
  (c) causing the pitching machine to deliver the ball from the delivery area to the hitting area.

8. The environmental arrangement for improving a batter's hitting of claim 7, wherein timing of steps (a) and (c) is such that the strobe light outputs strobing light visible from the hitting area during at least part of a time required for the ball to travel from the delivery area to the hitting area.

9. The environmental arrangement for improving a batter's hitting of claim 8, further comprising a device determining a trajectory of the ball after the ball is struck by a bat wielded by the batter.

10. The environmental arrangement for improving a batter's hitting of claim 5, further comprising a device determining a trajectory of the ball after the ball is struck by a bat wielded by the batter.

11. The environmental arrangement for improving a batter's hitting of claim 5, further comprising a laser tracking device projecting a customized strike zone in front of the batter.

12. An environmental arrangement for improving a batter's hitting, the environmental arrangement comprising:
  a ball;
  a batting cage having a hitting area and a delivery area from which the ball is delivered to the hitting area, the batting cage having general lighting, the general lighting being deactivated such that the batting cage is dark;
  a strobe light outputting strobing slight visible from the hitting area when the batter looks toward the delivery area and the ball is being delivered to the hitting area; and
  a speaker outputting sound audible from the hitting area.

13. The environmental arrangement for improving a batter's hitting of claim 12, wherein the ball has a glow-in-the-dark feature.

14. The environmental arrangement for improving a batter's hitting of claim 12, further comprising a UV light, and wherein the ball has a feature illuminated by the UV light.

15. The environmental arrangement for improving a batter's hitting of claim 12, further comprising a laser tracking device projecting a customized strike zone in front of the batter.

16. An environmental arrangement for improving a batter's hitting, the environmental arrangement comprising:
  a batting cage having a hitting area and a delivery area from which a ball is delivered to the hitting area;
  a strobe light outputting strobing slight visible from the hitting area when the batter looks toward the delivery area and the ball is being delivered to the hitting area;
  a speaker outputting sound audible from the hitting area;
  machine readable media;
  an input device;
  an output device;
  a processor in data communication with the machine-readable media, the input device, and the output device; and
  electronic instructions that, when executed by the processor, perform steps for at least one task selected from the group consisting of:
    (a) causing the strobe light to output the strobing light visible from the hitting area; and
    (b) causing the speaker to output the sound audible from the hitting area; and
  a plurality of lasers projecting a customized strike zone in a field of view of the batter in the hitting area.

17. The environmental arrangement for improving a batter's hitting of claim 16, further comprising a vapor screen.

* * * * *